United States Patent [19]

Shieh

[11] Patent Number: 5,098,539
[45] Date of Patent: Mar. 24, 1992

[54] GEL-CONTAINING MICROCAPILLARY COLUMN

[75] Inventor: Chia-Hui Shieh, San Lorenzo, Calif.

[73] Assignee: Beckman Instruments, Inc., Fullerton, Calif.

[21] Appl. No.: 688,182

[22] Filed: Apr. 19, 1991

[51] Int. Cl.$^5$ .................. G01N 27/26; B01D 57/02
[52] U.S. Cl. ..................... 204/182.8; 204/299 R
[58] Field of Search .................. 204/299 R, 182.8

[56] References Cited

U.S. PATENT DOCUMENTS

| | | | |
|---|---|---|---|
| 4,680,201 | 7/1987 | Hjerten | 427/230 |
| 4,865,706 | 9/1989 | Karger et al. | 204/182.8 |
| 4,865,707 | 9/1989 | Karger et al. | 204/182.8 |
| 4,997,537 | 3/1991 | Karger et al. | 204/182.8 |
| 5,015,350 | 5/1991 | Wiktorowicz | 204/180.1 |

OTHER PUBLICATIONS

Hjerten, S., "High-Performance Electrophoresis Elimination of Electroendosmosis and Solute Adsorption"; J. Chron., 347:191-198 (1985).

Cobb, K. A., et al; "Electrophoretic Separation of Proteins in Capillaries with Hydrolytically Stable Surface Structures"; Anal. Chem. 62:2478-2483 (1990).

*Primary Examiner*—John Niebling
*Assistant Examiner*—John S. Starsiak, Jr.
*Attorney, Agent, or Firm*—William H. May; Paul R. Harder; Richard P. Burgoon

[57] ABSTRACT

Disclosed is a gel-containing capillary column useful in high performance capillary electrophoresis. A preferred column includes a microcapillary having an interior cavity and a wall with an inner surface; a bifunctional agent comprising a positively charged amine adsorbed to the inner surface of the wall and an active functional group capable of copolymerizing with a polymeric gel material; and a polymer gel material filling the interior cavity of the microcapillary.

35 Claims, 4 Drawing Sheets

GEL-CONTAINING MICROCAPILLARY COLUMN

FIELD OF THE INVENTION

The present invention is generally directed to high performance capillary electrophoresis instruments and methods, and particularly to gel-containing microcapillary columns for high performance capillary electrophoresis.

BACKGROUND OF THE INVENTION

Electrophoresis is one of the most widely used separation techniques in the biologically-related sciences. Molecular species such as peptides, proteins, and oligonucleotides are separated by causing these species to migrate in a buffer solution under the influence of an electric field. This buffer solution normally is used in conjunction with a low-to-moderate concentration of an appropriate gelling agent such as, for example, agarose or polyacrylamide, to minimize the occurrence of mixing of the species being separated. Two primary separating mechanisms exist: a) separations based on differences in the effective charge of the analytes; and b) separations based on molecular size.

The first of these mechanisms is generally limited to low or moderate molecular weight materials, such as, for example, oligonucleotides. This is because the effective charges of high molecular weight materials become rather similar, making it difficult or impossible to separate them.

Separations based on molecular size are generally referred to as molecular "sieving". Molecular sieving relies upon gel matrices having controlled pore sizes as the separating medium. In such separating systems, if the effective charge of the analytes are the same, the separation results from differences in the abilities of the different size molecular species to penetrate through the gel matrix. Smaller molecules move relatively more quickly than larger ones through a gel of a give pore size.

Oligonucleotides and medium-to-high molecular weight polypeptides and proteins are commonly separated by molecular sieving electrophoresis, although in the case of proteins, charge and size can be used independently to achieve separations. In the case of proteinaceous materials, however, it is generally necessary to modify the materials to be separated so that they all have the same effective charges. This is commonly accomplished by employing an SDS-PAGE (sodium dodecyl sulfate-polyacrylamide gel electrophoresis) derivitization procedure, such as discussed in *Gel Electrophoresis of Proteins: a Practical Approach* (2nd edition, B.D. Hames & D. Rickwood, Eds., IRL Press, Oxford University Press, 1990. See also, *New Directions in Electrophoretic Methods*, J.W. Jorgenson Ampersand M. Phillips, Eds., Published by American Chemical Society, Washington, D.C., 1987. Both of these references are incorporated herein by reference.

Occasionally, it is desirable to separate proteinaceous materials under conditions which pose a minimal risk of denaturation of the protein. In such cases, some additives such as urea and SDS, which can cause denaturation of the protein, are avoided. Because of this, the resulting separations are predicated upon differences in both the molecular size and charge of the constituents of the materials.

Most electrophoretic separations are presently conducted in slabs or open beds. These separations are very difficult to automate or quantitate. Extremely high resolution separations of materials having different effective charges has been achieved by open tube free zone electrophoresis and isotachophoresis in narrow capillary tubes. In addition, bulk flow (i.e., the flow through the capillary tube of the electrophoresis buffer and the sample being analyzed) can be driven by electroosmosis to yield very sharp electropherograms peaks. Such high efficiency, open tube electrophoresis has not generally been applied to the separation of medium-to-high molecular weight oligonucleotides, however, because these materials have very similar effective charges, as previously noted. Furthermore, open-tube electrophoresis does not provide size selectivity for proteinaceous materials. Achieving high resolution separations of, e.g., oligonucleotides, is directly related to the gel containing microcapillaries utilized in the electrophoresis system. Accordingly, and because of the importance of high performance capillary electrophoresis as a separating technique in the biological sciences, significant attention has been paid to the gel-materials which are utilized in this technique.

Polymeric gel materials typically employed in high performance capillary electrophoresis are usually any crosslinked polymer which has a pore structure which can be adjusted by varying the amounts of monomer and crosslinking agent, as well as the reaction conditions. Preferred polymeric gel materials are based on acrylamide and N'-methylenebisacrylamide, N'-methylenebisacrylamide serving as a cross linking agent. Other crosslinking agents include N,N'-(1,2-dihydroxyethylene)-bisacrylamide, N,N'-diallyltartardiamide, N,N'-cystamine-bisacrylamide, and N-acryloyltris(hydroxymethyl) aminomethane. Gel polymerization is typically initiated by ammonium persulfate and N,N,N', N'-tetramethylethylenediamine (TEMED).

The pore size of polyacrylamide gels is dependent on total monomer concentration (% T) and on the concentration of crosslinker (% C). Pore size can be progressively increased by reducing % T at a fixed % C; however, very dilute gels are mechanically unstable and pore sizes greater than 80nm cannot be obtained. The alternative approach is to progressively increase % C at fixed % T where the increase in pore size is considered to be due to the formation of a bead-like structure rather than a 3-D lattice. In this procedure, stable gels of high pore size (about 200-250nm) can be obtained at 30% C N'-methylenebisacrylamide; however, at higher concentrations, the gels become hydrophobic and prone to collapse.

While the capillary gels themselves have been rather well defined and analyzed in the art, preparation of the capillary tubes including such gels has not been well defined. For example, conventional gel-containing microcapillary columns maintain the capillary gel within the column by way of covalent attachment of the gel to the column. See, for example, S. Hjerté, "High-Performance Electrophoresis Elimination of Electroosmosis and Solute Absorption." *J. Chrom.*, 347:191-198(1985); U.S. Pat. No. 4,865,707 (Karger et al) and U.S. Pat. No. 4,997,537 (Karger et al). The foregoing references are incorporated herein by reference. The gel-containing microcapillary columns described in the preceeding references suffer from at least the following problems: lot to lot reproducibility is unpredictable; the stability of the columns themselves is subject to failure after approximately 50-150 capillary runs; and the reaction time necessary for preparation of such columns can take as long as about 24 hours.

While capillary electrophoresis technology is generally directed towards the research environment, it has recently been suggested that this analytical technique has the potential for use as a clinical investigative technique. See "Capillary Electrophoresis: Tool for Clinical Diagnosis?", *Clin. Lab Letter* 12, 4: 1–2 (1991). While it is important in a research environment to ensure, e.g., lot to lot reproducibility and stability of the column, these concerns would be exacerbated in a clinical setting where patient analytical results require consistency from the analytical techniques utilized. Improved gel-filled capillary columns for electrophoresis which provides superior stability greater lot-to-lot reproducibility, improved resolution and shorter reaction times would be of great value to those fields that utilize such an analytical technique.

SUMMARY OF THE INVENTION

The foregoing needs are satisfied by the present invention which provides an improved gel-containing microcapillary for high performance electrophoresis. A gel-containing microcapillary according to the present invention includes a microcapillary, a bifunctional agent comprising at least one positively-charged amine and at least one active functional group, and a polymeric gel material. The bifunctional agent provides excellent adhesion of polymeric gel to the interior wall of the microcapillary. As used herein, the term "bifunctional" in reference to the agent means an agent capable of performing at least two functions, and is not a limitation as to the number of moieties included on the agent.

The bifunctional agent comprises at least one positively charged amino compound or a charged amino polymer and at least one active functional group. The positively charged amino is adsorbed onto the activated interior wall of the microcapillary. The active functional group is defined as a group including a carbon atom having at least one double bond. The active functional group is capable of copolymerizing with, e.g., acrylamide monomers. It, therefore, binds the gel material to the adsorbed bifunctional reagent.

Polyacrylamide gels which are coated to the interior capillary wall by the disclosed bifunctional agent require significantly less reaction time than gels which are covalently attached to the capillary wall. This is because adsorption, rather than covalent-binding, is utilized. Because the agent is adsorbed it, in effect, becomes a "part" of the interior wall of the capillary such that when the agent copolymerizes with the gel, the gel is securely affixed to the capillary.

Gel-containing microcapillary columns as disclosed herein may be prepared as follows: the interior surface of the capillary is first activated. The bifunctional agent is then introduced to the activated capillary whereby the positively-charged amine group is adsorbed onto the activated inner wall, and the activate functional group is exposed to the interior portion of the column. The microcapillary is next filled with a solution comprising at least one monomer with or without at least one crosslinking reagent; other materials, such as, e.g., a catalyst, may also be included in the solution. This solution is then allowed to polymerize within the microcapillary such that the polymerizing solution copolymerizes with the active functional group of the bifunctional agent. Ultimately, a polymeric matrix is formed which completely fills the microcapillary. By convention, at least one end of the gel-containing microcapillary is cut off cleanly and squarely, as a final step. The gel-containing microcapillary is then ready for use or for storage for subsequent use.

BRIEF DESCRIPTION OF THE DRAWINGS

The following drawings are presented for purposes of elucidation in conjunction with the Detailed Description of Preferred Embodiments of the invention.

DETAILED DESCRIPTION OF THE PREFERRED EMBODIMENTS

Figure 1:
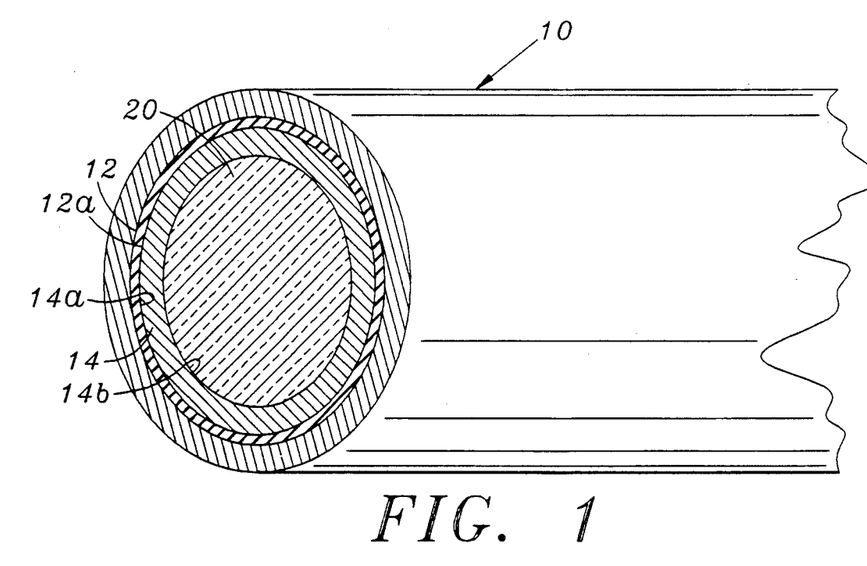
FIG. 1 provides a magnified perspective view of the end of a gel-containing microcapillary of the invention.

As depicted in FIG. 1, the gel containing microcapillary column in accordance with the present invention includes a microcapillary 10 including an activated layer 12; portion 12a is the inner most activated portion of microcapillary 10. Physically adsorbed to activated layer 12 is bifunctional agent 14 comprising a positively-charged amino compound or amino polymer 14a and an active functional group 14b; active functional group 14b is copolymerized with a polymeric gel 20 within the bore of microcapillary 10.

The bifunctional agent 14 has the following chemical structure:

where three of $R_1$, $R_2$, $R_3$ and $R_4$ can be independently selected from the group consisting of

, and H where
n is an integer between 0 and 10;
m is an integer between 0 and 5;

R is selected from the group consisting of the proviso being that at least one of $R_1$, $R_2$, $R_3$ and $R_4$ must comprise an active functional comprising a moeity selected from the group consisting of y is an integer between 1 and 5000, more preferably between 1 and 2000, and most preferably 1; and X is selected from the group consisting of flourine, chlorine, bromine, iodine and astatine.

In a most preferred embodiment of the bifunctional agent $R_1$, $R_2$ and $R_3$ are each $-(CH_2)_n CH_3$ where n is equal to 0 (i.e. $-CH_3$), $R_4$ is $(CH_2)_2=CH_2$, X is iodine ("I") and y is 1. Accordingly, a most preferred embodiment of the bifunctional agent can be represented as follows:

The particular materials used in the manufacture of microcapillary 10 are well known to those in the art and are typically selected with the proviso that the particular detection systems utilized in the electrophoresis can adequately function with such material. Such materials include, e.g., glass, alumina, beryllia, fused silica, and TEFLON. Preferably, the microcapillary is made of fused silica. Preferably, the internal diameter of the microcapillary is between about 10 and about 2000 microns, more preferably between about 10 and about 200 microns, and most preferably about 100 microns.

The interior portion 12a of microcapillary 10 is pretreated prior to introduction of the bifunctional agent thereto. Such pretreatment "activates" interior portion 12a, thus providing a negative charge thereto. Pretreatment is preferably accomplished by filling microcapillary 10 with 1N HCl for 10 minutes, followed by 1N NaOH for 10minutes, followed by deionized water-washing for 10 minutes. This standard procedure efficiently activates the microcapillary for adsorption purposes.

The agent is introduced to the capillary as a bifunctional agent solution. The bifunctional agent solution is most preferably an aqueous solution. However, polar solvents such as, for example, dioxane, dimethylformamide, acetane, methanol, or ethanol may be used. Preferably, the solution contains between about 1% and about 80% (by volume) of the bifunctional agent, more preferably between about 10% and about 50%, and most preferably about 30%. The pH of the bifunctional agent solution is preferably between about 4 and about 12, more preferably between about 5 and about 9, and most preferably about 8. However, when any of $R_1$, $R_2$, $R_3$ or $R_4$ is/are H, then the pH of the bifunctional agent solution is less than about 7.0 so that protonation of the amine can occur.

The bifunctional agent solution is then introduced into the activated microcapillary and flushed through it for between about 1 minute and about 60 minutes, more preferably for between about 15 minutes and 45 minutes, and most preferably about 30 minutes. After this period of time, the bifunctional agent is adsorbed to the microcapillary. Preferably, adsorption takes place at about room temperature, although temperatures of 20-35° C. are acceptable. After the bifunctional agent has reacted with the microcapillary inner wall, the inner portion of the microcapillary is ready for introduction of a polymeric gel material thereto.

Polymeric gel materials applicable to capillary electrophoresis are well known. The polymeric gel material 20 utilized can be any polymer which has a pore structure which can be varied—the gel may or may not be crosslinked. Preferably, the polymeric gel is a crosslinked polymer whose pore structure is varied based upon the amounts of monomer and crosslinking agent added to form the gel, as well as varying the reaction conditions. As previously indicated, the variations in the total concentration of the monomer and the crosslinking agent are generally expressed as % T and % C, respectively. For the monomer acrylamide and the crosslinking agent N,N'-methylenebisacrylamide system which is most preferably utilized in the invention, % T and % C are derived as follows:

$$\% T = \frac{\text{grams of acrylamide} + \text{grams of bisacrylamide}}{100 \text{ millimeters of solvent}}$$

$$\% C = \frac{\text{grams of bisacrylamide} \times 100}{\text{grams of bisacrylamide} + \text{grams of acrylamide}}$$

See, Hjerten, *Chromatographic Review* 5, 9:122-219 (1967) which is incorporated herein by reference. The concentrations of monomer and any crosslinking agent are determined according to the porosity of the polymeric matrix desired. As noted previously, the reaction is preferably initiated with ammonium persulfate. However, the concentration of initiator (and polymerization catalyst, if any) in the reaction mixture can be determined experimentally. This can be accomplished by preparing test solutions containing the desired % T and % C, but varying the amount of initiator (and polymerization catalyst) utilized. Preferably, % T is from about 1 to about 30, more preferably from about 3 to about 15, and most preferably about 12. Preferably, % C is from about 0 to about 15, more preferably from about 1 to about 6, and most preferably about 2.

After % T and % C have been determined, a fresh mixture of polymerization mixture is prepared and injected into the microcapillary tube, typically by means of a syringe. The formation of bubbles is to be avoided as this can lead to a useless gel-filled microcapillary column. When the microcapillary tube has been filled with the polymerization mixture, the ends of the microcapillary are plugged or capped, and such plugging or capping is maintained on the microcapillary while the polymerization reaction occurs.

The polymerization reaction is most preferably carried out at about room temperature and for at least about 2 hours, more preferably overnight. However, polymerization temperatures and times can vary depending on the gel material utilized.

As a final step, after the polymerization reaction is completed, the plugs or caps are removed from the ends of the microcapillary and at least one end of the microcapillary is cut off cleanly and squarely. The object of such cutting is to leave a smooth surface of gel material exposed at the end of the microcapillary—it is to this end that the sample to be analyzed can be introduced. The gel-filled microcapillary column may then be placed in suitable electrophoresis apparatus. The column can be checked on the apparatus by applying a very low electric field (about 100 to 150 volts/cm) for about one hour to the capillary. An improperly prepared column will generate a "noisy" baseline or a zero current condition.

High resolution capillary electrophoresis using the prepared gel-filled microcapillary columns includes the steps of electrophoretically injecting an aliquot of a sample containing constituents to be separated into the column of the invention, applying an electric field of between about 50 and about 600 volts/cm, allowing a current preferably less than about 2 to about 50 microampers to pass through the microcapillary, and instrumentally detecting and measuring the separated analytes sequentially as they migrate past an on-line detector. Typically, the measurements are presented as electropherogram peaks, where each sample constituent that is detected has a defined peak based upon the flow rate of the constituent past the detector as well as the amount of the constituent in the sample.

The improved gel-filled microcapillary columns containing a bifunctional agent comprising a positively charged amine and an active functional group exhibit excellent stability and have resolving power (i.e. the ability to separate the sample constituents) equal to or better than previous columns. Additionally, such columns exhibit excellent run-to-run, batch-to-batch reproducibility. The present columns require only about 30 minutes for preparation of the adsorbed-bifunctional agent microcapillary, as opposed to approximately 24 hours required for covalently attaching materials which bind the gel to the microcapillary.

The following examples are presented for illustrative purposes only and are not intended, nor should they be construed to be, a limitation on the foregoing disclosure or the claims to follow.

EXAMPLES

Capillary electrophoresis of the samples described in the following Examples was performed on a Beckman Instruments, Inc. PACE TM high performance capillary electrophoresis system (Beckman Instruments, Inc., Fullerton, CA. Model No. #2000). Data analysis was performed on System Gold TM software (Beckman Instruments, Inc.). The PACE TM high performance capillary electrophoresis system contains built-in 214, 254, 280 and 415nm narrow-band filters for on-line detection. The detection window was located approximately 6.5 cm from the column outlet.

Samples were placed on the inlet tray of the above-referenced capillary electrophoresis system. Samples were automatically injected into the gel-filled microcapillary tube by the electrokinetic method for 1.5 seconds at 75 kV.

The electrophoresis buffer was 7M urea in 10mM tris-hydroxymethyl amino methane—250mM borate, pH 8.3.

EXAMPLE I

Preparation of Bifunctional Agent 106 g of sodium carbonate (J. T. Baker, Phillipsburg, N.J., Cat. #3604), 37.5ml of alkyl amine (Aldrich Chemical, Milwaukee, Wis., Cat. #24107-5), and 200ml of methanol (B&J, McGaw Park, Il., Cat. #230) were stirred in a 1L round bottom flask. 124.5 ml of iodomethane (Aldrich, Cat. #I-778-0) in 50ml of ethanol was slowly added to the flask by a dropping funnel. The reaction mixture was stirred overnight (18 hours). The methanol was evaporated on a rotavap. 15 ml of iodomethane was then added to the flask, followed by 10 minutes of shaking. 200 ml of water and 20 ml of tetrahydrofuran (B&J, Cat. #340) was added to the solution and stirred for 20 minutes. The sodium carbonate was then filtered, and the aqueous layer was collected and filtered through a 0.2 micron membrane filter.

The resulting solution included a quarternary alkyl amine bifunctional agent.

EXAMPLE II

Preparation of Gel Columns

A 65 cm, 100 micron i.d. microcapillary column (Polymicro, Phoenix, Ariz., #TSP100375) was pretreated by introducing to the interior of the microcapillary 1N hydrochloric acid for 10 minutes, followed by 1N sodium hydroxide for 10 minutes, followed by a deionized water rinse for 10 minutes. After pretreatement, the gel column was coated with the bifunctional agent of Example I by placing the solution in the capillary for 30 minutes.

For 7M urea gel, 1.2 g of ultrapure acrylamide (ICN, Irvine, Calif. Cat. #814320) was dissolved in 10 ml of 7M urea, tris-hydroxymethyl amino-methane-borate buffer ("tris-borate" buffer) (7M urea, 100 mM tris, 250 mM borate, pH 8.3). The acrylamide solution was then filtered through a 0.2 micron nylon filter. 2ml acrylamide solution, 2 microliters of 10% ammonium persulfate (BRL, Gaithersburg, Md. Cat. #5523) in deionized water, and 2 microliters N,N,N',N'tetramethylenediamine (BRL, Cat. #5524 UB) were mixed and poured into the coated microcapillary column using 10 psi helium gas; after 3½ minutes the pressure was decreased to 5 psi followed by continued, gradual decrease such that after 5 minutes the pressure was 0 psi. The microcapillary ends were capped and stored at room temperature for 18 hours for polymerization. The gel-filled microcapillary tubes were then stored until used at 4–8° C.

For a gel column not containing 7M urea, the foregoing procedure was followed, the exception being that the acrylamide was dissolved in tris-borate buffer (100mM tris, 100mM borate, pH 8.3).

EXAMPLE III

Separation of Poly d(A) Oligomers 7M Urea Gel Column

Poly d(A) 25–30mers and 40–60mers (Pharmacia, part #27-7986-01 and #27-7988-01, respectively) were separated on the aforementioned PACE TM high performance capillary electrophoresis system using the 7M urea gel-filled microcapillary column of Example II. The microcapillary had a 47 cm total length, 40 cm effective length and an i.d. of 100 μm. The injection was accomplished with 75 kV for 1.5 seconds of 1.50 OD units/ml of sample. The analytical run was accomplished with 11.1 kV at 30° C.

Figure 2:
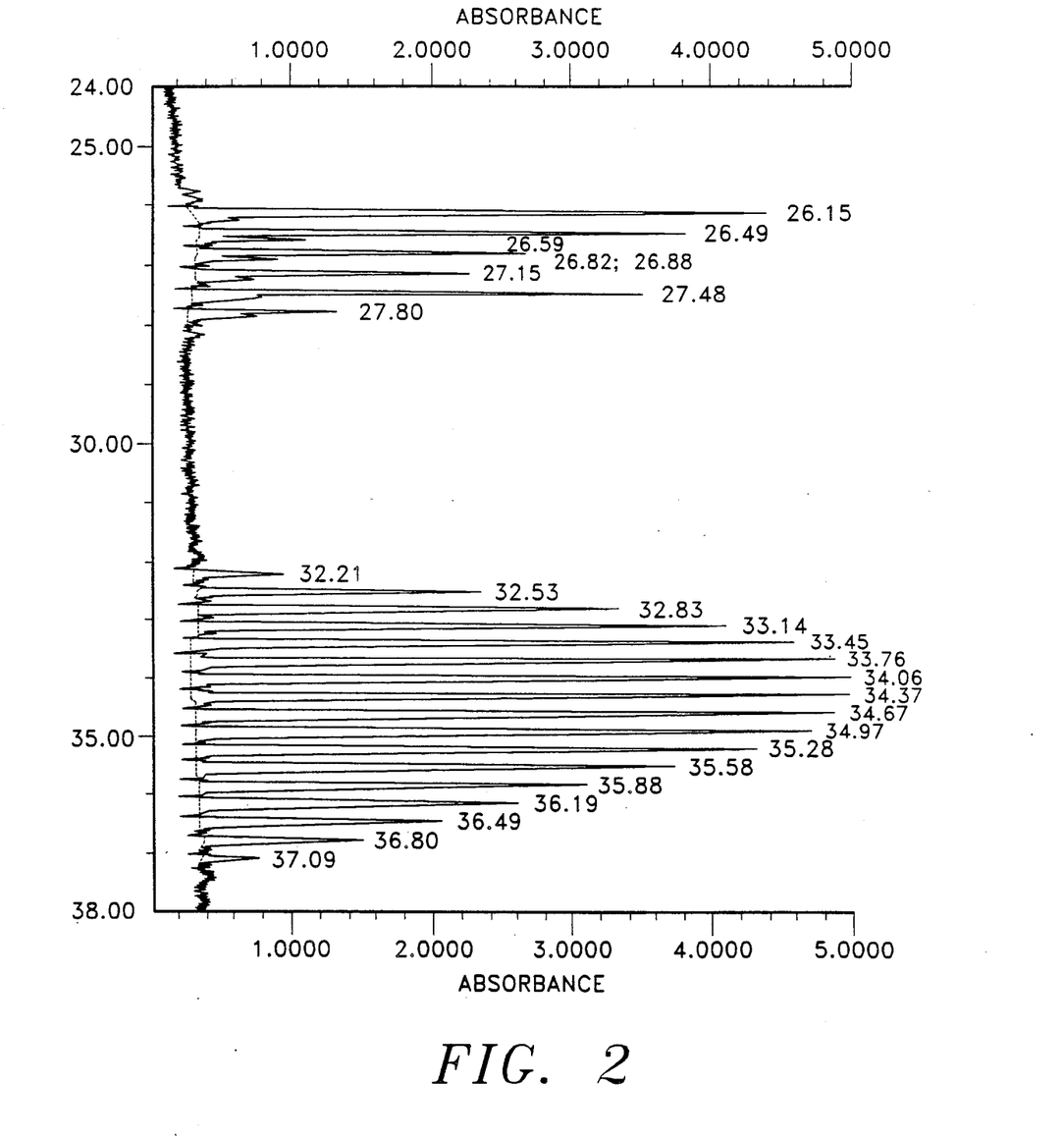
FIG. 2 is an electropherogram of the separation of a poly d(A) 25–30mer and a poly d(A) 40–60mer using 7M urea polyacrylamide gel-containing microcapillary in accordance with the present disclosure.

Analytical results are presented in FIG. 2 where absorbance ($\times 10^{-3}$) is plotted against the horizontal axis, migration time is plotted against the vertical axis and the poly d(A) 25–30 mer appears in time before the poly d(A) 40–60 mer.

EXAMPLE IV Separation of Poly d(A) Oligomers - Non-Urea Gel Column

Figure 3:
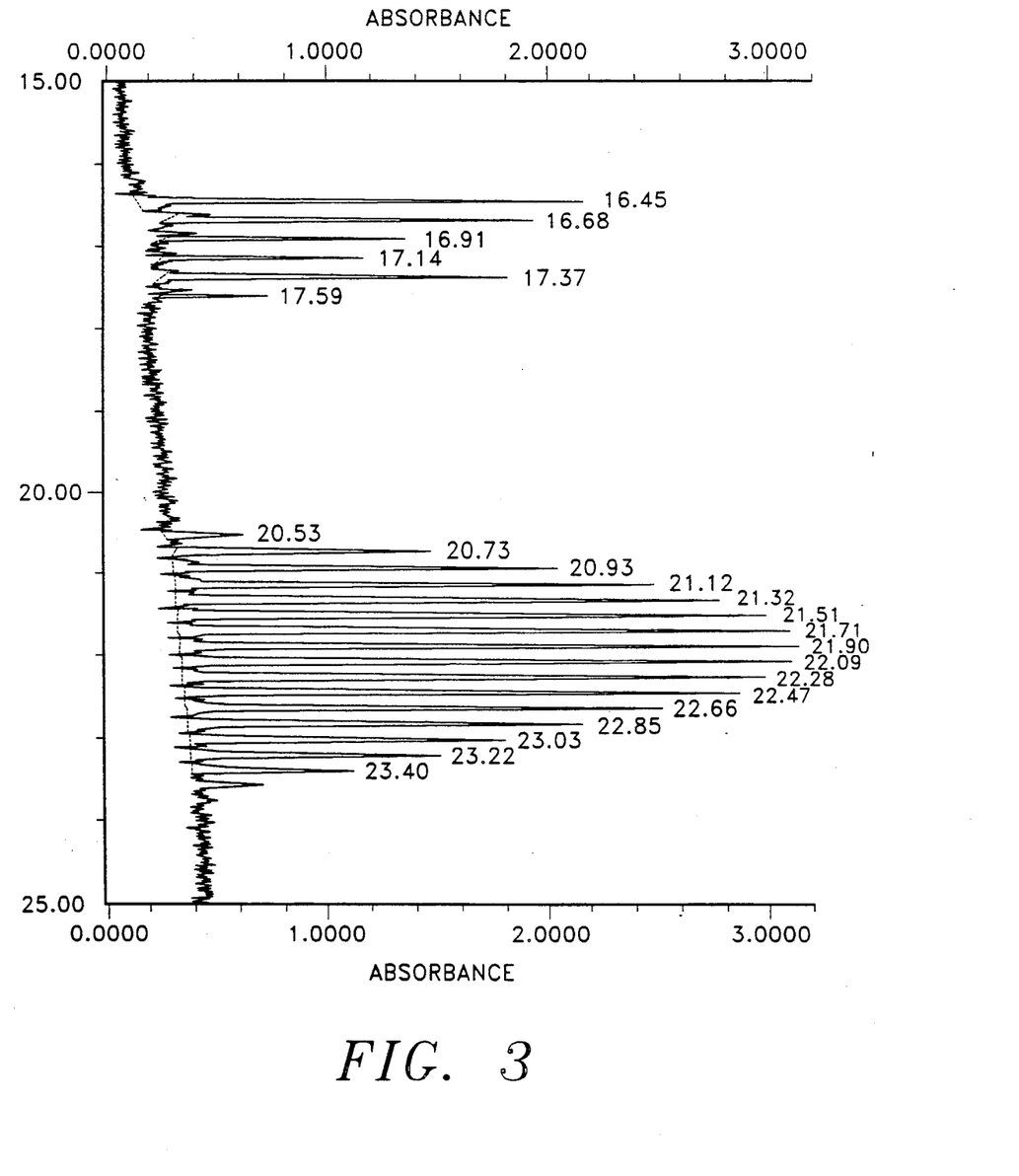
FIG. 3 is an electropherogram of the separation of the same oligomers of FIG. 2 using a polyacrylamide gel-containing microcapillary in accordance with the present disclosure.

The same oligomers of Example III were separated in accordance with the procedure of Example III using the non-urea gel-filled microcapillary column of Example II. Analytical results are presented in FIG. 3 in accordance with the description in Example III.

EXAMPLE V

Separation of Poly d(T) Oligomers - 7M Urea Gel Column

A mixture of poly d(T) 20 mer and 40 mer (Pharmacia, part #28-8610-01) was separated in accordance with the procedure of Example III using the 7M urea gel-filled microcapillary column of Example II. Analytical results are presented in FIG. 4 in accordance with the description of Example III, the description being that the poly d(T) 20 mer appears in time before the poly d(T) 40 mer.

EXAMPLE VI

Stability Study - 7M Urea Gel Column

Figure 4:
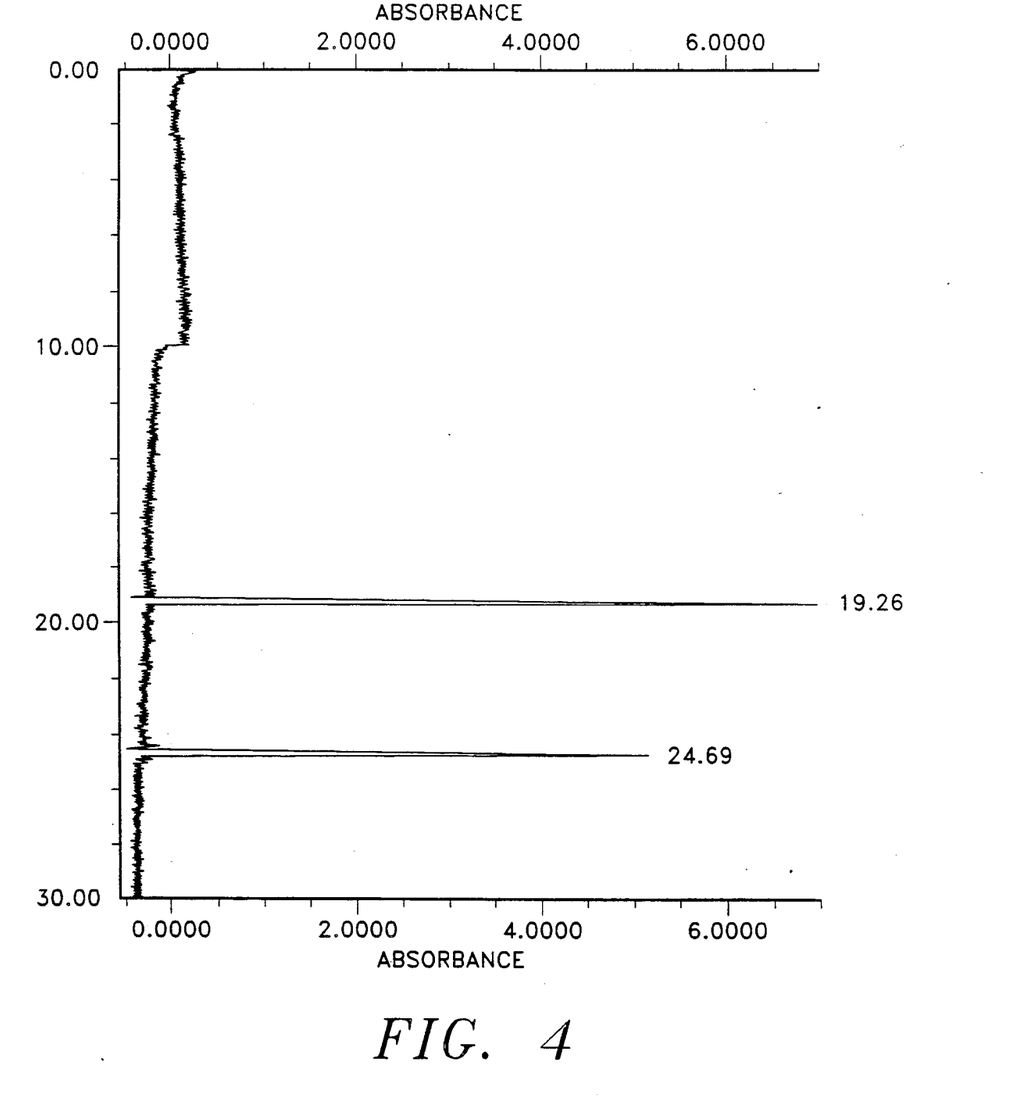
FIG. 4 is an electropherogram of the separation of a poly d(T) 20-mer and a poly d(T) 40-mer using 7M urea polyacrylamide gel-containing microcapillary in accordance with the present disclosure.
Figure 5:
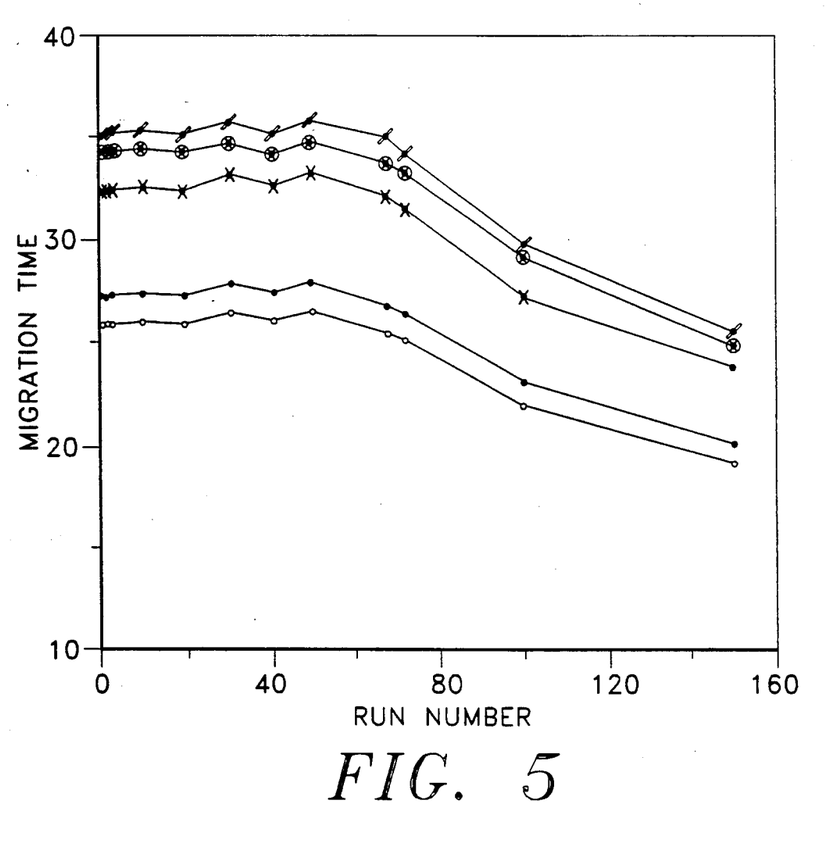
FIG. 5 is a graphic representation of the stability of a 7M urea polyacrylamide gel-containing microcapillary in accordance with the present disclosure as determined "Migration Time" vs. "Injections".

Migration times for poly d(A) 25, 29, 41, 47 and 50mers were obtained across a number of injections of the oligomers using the 7M urea gel-filled microcapillary column of Example II. Results are depicted in FIG. 5. The results demonstrate that the gel-filled microcapillary column is stable for at least about 100 injections. In FIG. 4, the following symbols are used: poly d(A) 25 −°; poly d(A) 29 −•; poly d(A) 41 x; poly d(A) 47 - (x); and poly d(A) 50 - /.

The bifunctional agent of the present invention provides for adsorption of the amine-portion of the reagent to the microcapillary within about 30 minutes after the agent is introduced thereto. The active functional group is then capable of copolymerizing with the polymerizing gel material added to the microcapillary. The foregoing examples demonstrate that a gel-filled microcapillary column incorporating the bifunctional agent has excellent resolving power and are stable for at least about 100 injections. The bifunctional agent requires only about 30 minutes for adsorption to the capillary inner wall, as opposed to about 24 hours required by the prior art covalent attachment. Accordingly, the present bifunctional agent offers several additional advantages over previous gel-filled microcapillary columns.

What is claimed is:

1. A gel-containing microcapillary column comprising;
    (a) a microcapillary having an interior cavity defined by a wall with an inner surface;
    (b) a bifunctional agent adsorbed to the inner surface of the wall, said bifunctional agent comprising at least one positively charged amine and at least one active functional group; and
    (c) a polymeric gel in the interior cavity of the microcapillary.

2. The microcapillary of claim 1 wherein the active functional group comprises at least one carbon atom attached to a second atom by a double bond.

3. The microcapillary of claim 1 wherein the active functional group comprises at least one carbon atom attached to a second atom by a triple bond.

4. The microcapillary of claim 1 wherein the bifunctional agent is represented by the following structure:

$R_1$, $R_2$, and $R_3$ are each selected independently from the group consisting of where
n is an integer between 0 and 10,
m is an integer between 0 and 5,
R is selected from the group consisting of $-(CH_2)_n$, $-CH_3$ and
$R_4$ is an active functional group;
y is an integer between 1 and 5000; and
X is selected from the group consisting of fluorine, chlorine, bromine, iodine and astatine.

5. The microcapillary of claim 4 wherein $R_1$, $R_2$ and $R_3$ are each $-(CH_2)_n CH_3$.

6. The microcapillary of claim 5 wherein n is 0.

7. The microcapillary of claim 4 wherein the active functional group comprises a moiety selected from the group consisting of

8. The microcapillary of claim 4 wherein the active functional group comprises a —C═C— moiety.

9. The microcapillary of claim 4 wherein y is an integer between 1 and 2000.

10. The microcapillary of claim 4 wherein y is 1.

11. The microcapillary of claim 4 wherein X is

12. The microcapillary of claim 1 wherein the bifunctional agent is represented by the following structure:

13. The m1microcapillary of claim 1 wherein the polymeric gel further comprises a copolymer of acrylamide and at least one crosslinking agent.

14. The microcapillary of claim 1 wherein the microcapillary is selected from the group consisting of glass, alumina, beryllia, fused silica and TEFLON.

15. The microcapillary of claim 1 wherein the microcapillary is fused silica.

16. A gel containing microcapillary comprising
  a) a microcapillary having an interior cavity-space and a wall with an inner surface;
  b) a bifunctional agent represented by the following structure:

where the positively charged amine is adsorbed to the inner surface of the wall; and
  c) a polymeric gel filling the interior cavity of the microcapillary.

17. The microcapillary of claim 16 wherein the polymeric gel further comprises a copolymer of acrylamide and at least one crosslinking agent.

18. The microcapillary of claim 16 wherein the gel is a copolymer of acrylamide monomer and N,N′-methylenebisacrylamide crosslinking agent.

19. The microcapillary of claim 16 wherein the microcapillary is fused silica.

20. A method of performing capillary electrophoresis comprising:
  (a) injecting an aliquot of a sample containing constituents to be separated into a gel containing microcapillary column, the column comprising
    (i) a microcapillary having an interior cavity defined by a wall with an inner surface,
    (ii) a bifunctional agent adsorbed to the inner surface of the wall, said bifunctional agent comprising at least one positively charged amine and at least one active functional group, and
    (iii) a polymeric gel in the interior cavity of the microcapillary,
  (b) applying an electric field of at least about 50 volts per centimeter to the microcapillary column;
  (c) separating the sample into its constituent parts; and
  (d) detecting the constituents of the sample sequentially.

21. The microcapillary of claim 20 wherein the active functional group comprises at least one carbon atom attached to a second atom by a double bond.

22. The microcapillary of claim 20 wherein the active functional group comprises at least one carbon atom attached to a second atom by a triple bond.

23. The microcapillary of claim 20 wherein the bifunctional agent is represented by the following structure:

$R_1$, $R_2$, and $R_3$ are each selected independently from the group consisting of where
n is an integer between 0 and 10,
m is an integer between 0 and 5,
R is selected from the group consisting of $-(CH_2)_n$, $-CH_3$ and

$-(CH_2)_n$, $-CH_3$ and ;

$R_4$ is an active functional group;
y is an integer between 1 and 5000; and
X is selected from the group consisting of fluorine, chlorine, bromine, iodine and astatine.

24. The microcapillary of claim 23 wherein $R_1 R_2$ and $R_3$ are each $-(CH_2)_n\ CH_3$.

25. The microcapillary of claim 24 wherein n is 0.

26. The microcapillary of claim 23 wherein the active functional group comprises a moiety selected from the group consisting of

27. The microcapillary of claim 23 wherein the active functional group comprises a —C=C— moiety.

28. The microcapillary of claim 23 wherein y is an integer between 1 and 2000.

29. The microcapillary of claim 23 wherein y is 1.

30. The microcapillary of claim 23 wherein X is iodine.

31. The microcapillary of claim 21 wherein the bifunctional agent is represented by the following structure:

32. The microcapillary of claim 20 wherein the polymeric gel further comprises a copolymer of acrylamide and at least one crosslinking agent.

33. The microcapillary of claim 20 wherein the microcapillary is selected from the group consisting of glass, alumina, beryllia, fused silica and TEFLON.

34. The microcapillary of claim 20 wherein the microcapillary is fused silica.

35. The method of claim 20 wherein the bifunctional agent is represented by the following structure:

where the positively charged amine is adsorbed to the inner surface of the wall and the active functional group $-(CH_2)_2=CH_2$ is copolymerized with the polymeric gel.

* * * * *

UNITED STATES PATENT AND TRADEMARK OFFICE
CERTIFICATE OF CORRECTION

PATENT NO. : 5,098,539

DATED : March 24, 1992

INVENTOR(S) : Chia-Hui Shieh

It is certified that error appears in the above-indentified patent and that said Letters Patent is hereby corrected as shown below:

In column 1, line 55, the word "Ampersand" should be replaced with the symbol "&".

In column 4, lines 52-65, the second appearance of the moiety "$-(CH_2)_n-\overset{\overset{O}{\|}}{C}-R$" should be deleted, and In column 4, lines 52-65, the moiety "$-(CH_2)_n-\overset{\overset{O}{\|}}{C}-O-R$" should be changed to -- $-(CH_2)_n-\overset{\overset{O}{\|}}{C}-O-R$ --.

Col. 10, and 12, line 22 and 13:

In claims 4 and 23, the second appearance of the moiety "$-(CH_2)_n-\overset{\overset{O}{\|}}{C}-R$" should be deleted.

Col. 10, and 12, lines 34 and 26:

In claims 4 and 23, the first appearance of the R moieties "$-(CH_2)_n$" and "$-CH_3$" should be deleted.

UNITED STATES PATENT AND TRADEMARK OFFICE
CERTIFICATE OF CORRECTION

PATENT NO. : 5,098,539
DATED : March 24, 1992
INVENTOR(S) : Chia-Hui Shieh

It is certified that error appears in the above-indentified patent and that said Letters Patent is hereby corrected as shown below:

Col 10 and 12, lines 37 and 30:
In claims 4 and 23, the moiety "$-(CH_2)_n-\overset{\text{"}}{\underset{O}{C}}-O-R$" should be changed to -- $-(CH_2)_n-\underset{O}{\overset{\text{"}}{C}}-O-R$ --.

Signed and Sealed this

Fifth Day of July, 1994

BRUCE LEHMAN

Attest:

Attesting Officer

Commissioner of Patents and Trademarks